United States Patent [19]

Alderdice

[11] Patent Number: 4,687,772
[45] Date of Patent: Aug. 18, 1987

[54] METHOD FOR IMPROVEMENT OF SHORT TERM MEMORY

[75] Inventor: Marc T. Alderdice, Evansville, Ind.

[73] Assignee: Bristol-Myers Company, New York, N.Y.

[21] Appl. No.: 916,661

[22] Filed: Oct. 7, 1986

[51] Int. Cl.⁴ .......................................... A61K 31/505
[52] U.S. Cl. ..................................................... 514/273
[58] Field of Search ....................................... 514/273

[56] References Cited

U.S. PATENT DOCUMENTS

| | | | |
|---|---|---|---|
| 3,717,634 | 2/1973 | Wu et al. | 544/230 |
| 3,976,776 | 8/1976 | Wu et al. | 514/252 |
| 4,182,763 | 1/1980 | Casten et al. | 514/252 |
| 4,438,119 | 3/1984 | Allen et al. | 514/252 |

OTHER PUBLICATIONS

Wu, et al., *J. Med. Chem.*, 15, 477–479 (1972).
Allen, et al., *Arzneim. Forsch.* 24, No. 6, 917–922 (1974).
Sathananthan, et al., *Current Therapeutic Research*, 18/5, 701–705 (1975).
Friedman, et al., *New England Journal of Medicine*, 304: 1490–1491 (1981) (4/10).
Wesseling, et al., *New England Journal of Medicine*, 210: 985–989 (1984) (4/15).
Davis, et al., *American Journal of Psychiatry*, 139: 1421–1424, (1981) (4/21).
Davis, et al., *Science*, 201: 274–276 (1978).
Sitaran, et al., *Science*, 201: 274–276 (1978).
Shader, et al., *Journal American Geriatric Society*, 22: 107–113 (1974) (5/4).

Primary Examiner—Stanley J. Friedman
Attorney, Agent, or Firm—Richard P. Ryan

[57] ABSTRACT

Buspirone and its pharmaceutically acceptable salts are useful in the clinical improvement of short term memory.

7 Claims, 2 Drawing Figures

METHOD FOR IMPROVEMENT OF SHORT TERM MEMORY

BACKGROUND OF THE INVENTION

This invention is concerned with a drug bioaffecting, body-treating process which employs the pyrimidine compound 8-[4-[4-(2-pyrimidinyl)-1-piperazinyl]-butyl]-8-azaspiro[4.5]decane-7,9-dione or a pharmaceutically acceptable acid addition salt thereof (class 424, subclass 251).

This pyrimidine compound with which the present invention is concerned has the following structural formula

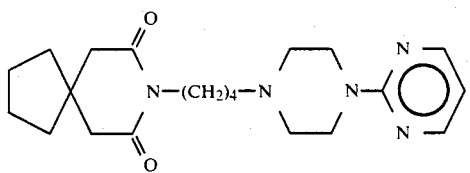

and is known as buspirone. The hydrochloride salt has been referred to in the prior art as MJ 9022-1 and as buspirone hydrochloride. Other acid addition salts thereof are named by combining "buspirone" with the appropriate word to define the acid from which it is prepared as in "buspirone hydrochloride". The latter is the United States Adopted Name (USAN); refer to *J. American Med. Assoc.* 225, 520 (1973).

The synthesis of the compound and the disclosure of its psychotropic properties are described in the following patents and publications.

1. Y. H. Wu, et al., *J. Med. Chem.*, 15, 477 (1972).
2. Y. H. Wu, et al., U.S. Pat. No. 3,717,634 which issued Feb. 20, 1973.
3. L. E. Allen, et al., *Arzneim. Forsch.*, 24, No. 6, 917–922 (1974).
4. G. L. Sathananthan, et al., *Current Therapeutic Research*, 18/5, 701–705 (1975).
5. Y. H. Wu, et al., U.S. Pat. No. 3,976,776, issued August 24, 1976.

The use of buspirone hydrochloride as a novel anti-anxiety agent for the treatment of neurotic patients is described in G. P. Casten, et al., U.S. Pat. No. 4,182,763, issued Jan. 9, 1980. A New Drug Application (NDA) has been approved by the U.S. Food & Drug Administration for the use of buspirone in the treatment of general anxiety disorder.

Buspirone has also been disclosed as being useful in the treatment of other disorders. Allen, et al., U.S. Pat. No. 4,438,119, issued Mar. 20, 1984, disclosed buspirone's use in alleviation of extrapyramidal motor disorders.

Currently, other clinical studies are being conducted to provide support for the use of buspirone in panic disorders and in the treatment of sexual dysfunction. The use of buspirone for alleviation of panic disorders has been disclosed in U.S. Ser. No. 791,182, which is currently pending; and buspirone's use in treating sexual dysfunction has been disclosed in U.S. Ser. No. 825,826, also currently pending The present invention can be distinguished from the above prior art in that it is directed to a use which is unexpected and which can be distinguished from its application in the above-described disorders. Usefulness in any or all of these clinical disorders would not suggest or in any way make obvious the use of buspirone in short-term memory improvement.

Other drugs have been reported to be useful in memory enhancement although there is no drug which is presently accepted as a standard for this use. The general area is further complicated as to applicability of improvement, i.e. whether any improvement represents a normalization of cognitive function in an impaired population, above normal enhanced performance in an unimpaired population, or an improvement in memory regardless of degree of impairment. In any event, pharmacological agents have been reported to result in cognitive improvement in various populations of people who have been treated. Some examples of these populations are geriatric subjects, patients with Alzheimer's disease, demented patients, cognitively impaired patients, anxious patients, and normal subjects. Substances used in these studies have comprised cholinergic pre-synaptic agents such as choline, piracetam, 4-aminopyridine, and lecithin; synaptic agents such as physostigmine; and post-synaptic agents such as arecholine. Miscellaneous agents such as vasopressin, and naloxone; and vasodilators such as cyclospasmol and hydergine have also been reported. None of these substances would suggest the use of buspirone for improvement of memory.

The following specific references may be considered to be representative of the prior art concerning reports of memory enhancement by pharmacologic agents.

Friedman, et al., *New England Journal of Medicine*, 304;1490–1491 (1981) reported a study in ten patients with mild to moderate memory impairment which were treated with choline and piracetam for seven days. A mean improvement of 70% in verbal memory retrieval was obtained.

Wesseling, et al., *New England Journal of Medicine*, 310:985–989 (1984) reported a study in 14 patients with Alzheimer's disease who were given 4-aminopyridine for 12 weeks in a double-blind, randomized, cross-over study. Treatment with 4-aminopyridine resulted in significant improvement in recent-memory testing for patients.

Davis, et al., *American Journal of Psychiatry*, 139:1421–1424 (1981) reported improvement in recognition memory testing for 10 Alzheimer's disease patients who received physostigmine. In normal subjects, however, Davis, et al., *Science*, 201:272–274 (1978) reported that physostigmine significantly enhanced long-term memory processes but not short-term memory processes.

Sitaram, et al., *Science*, 201:274–276 (1978) reported that arecholine significantly enhanced serial learning in normal human subjects.

Shader, et al., *Journal American Geriatric Society*, 22:107–113 (1974) reported that hydergine-treated patients showed a small but significant improvement in recent memory.

In summary, there exists nothing in the prior art that would teach or suggest that buspirone and its pharmaceutically acceptable salts would be useful in improving short-term memory.

SUMMARY OF THE INVENTION

The process of the present invention is intended for improving short-term memory. The process essentially involves administration of buspirone, or a pharmaceutically acceptable acid addition salt thereof, to one in need of such treatment. For use in the instant process, oral administration of buspirone hydrochloride from about 20 to 60 mg per day in divided doses is anticipated as being the preferred dosage regimen. Pharmaceutically acceptable acid addition salts of buspirone and methods of pharmaceutical formulation are described in the above patents of Wu, et al., U.S. Pat. No. 3,717,634 and Casten, et al., U.S. Pat. No. 4,182,763, which are incorporated by reference herein in their entirety.

BRIEF DESCRIPTION OF THE FIGURE

FIG. 1 graphically demonstrates enhancement of short-term memory for the high dose (20–30 mg per day) buspirone group. Scores are also displayed for the other three treatments which were: low dose buspirone (15–20 mg per day); diazepam (15–20 mg per day); and placebo. The comparative measurements made represent deviation of the mean score for a treatment group from its baseline (pre-study) score. The recall test scores were obtained at pre-study and study days 1, 4, and 7.

DETAILED DESCRIPTION OF THE INVENTION

Improvement of short term memory following administration of buspirone was discovered in analyzing results of a placebo-controlled study of the short-term effects of buspirone and diazepam in anxious subjects. The study was a 7-day, double-blind, randomized, parallel-group study involving four treatment groups, with 10 patients per group. Subjects were randomized to one of the four groups: placebo, diazepam (15–20 mg/day, given in three divided doses); low dose buspirone (15–20 mg/day, given in three divided doses); and high dose buspirone (20–30 mg/day, given in two or three divided doses). All groups ended up with 10 evaluable patients except for the high dose buspirone group which had only 9.

All subjects utilized in the study were out patients who manifested at least moderate symptoms of anxiety and met requirements for generalized anxiety disorder according to DSM-III diagnostic criteria, which is understood to one skilled in the pertinent art of the clinical study of psychotropic agents. Various tests related to psychomotor function and behavior were performed at baseline, which was from a week to 3 days prior to initiation of the study, and at days 1, 4, and 7 of the study. The pertinent memory tests were given at these time points to each patient.

Both immediate and delayed recall were tested by reading lists of 16 words each to subjects and asking them to repeat as many words as they could recall, either immediately (immediate recall) or 20 minutes after the list was read (delayed recall). The testing period schedule was governed in the design of the study by the consideration that these memory tests can be performed and evaluated accurately if they are administered no more often than once a day every three days.

Figure 1:
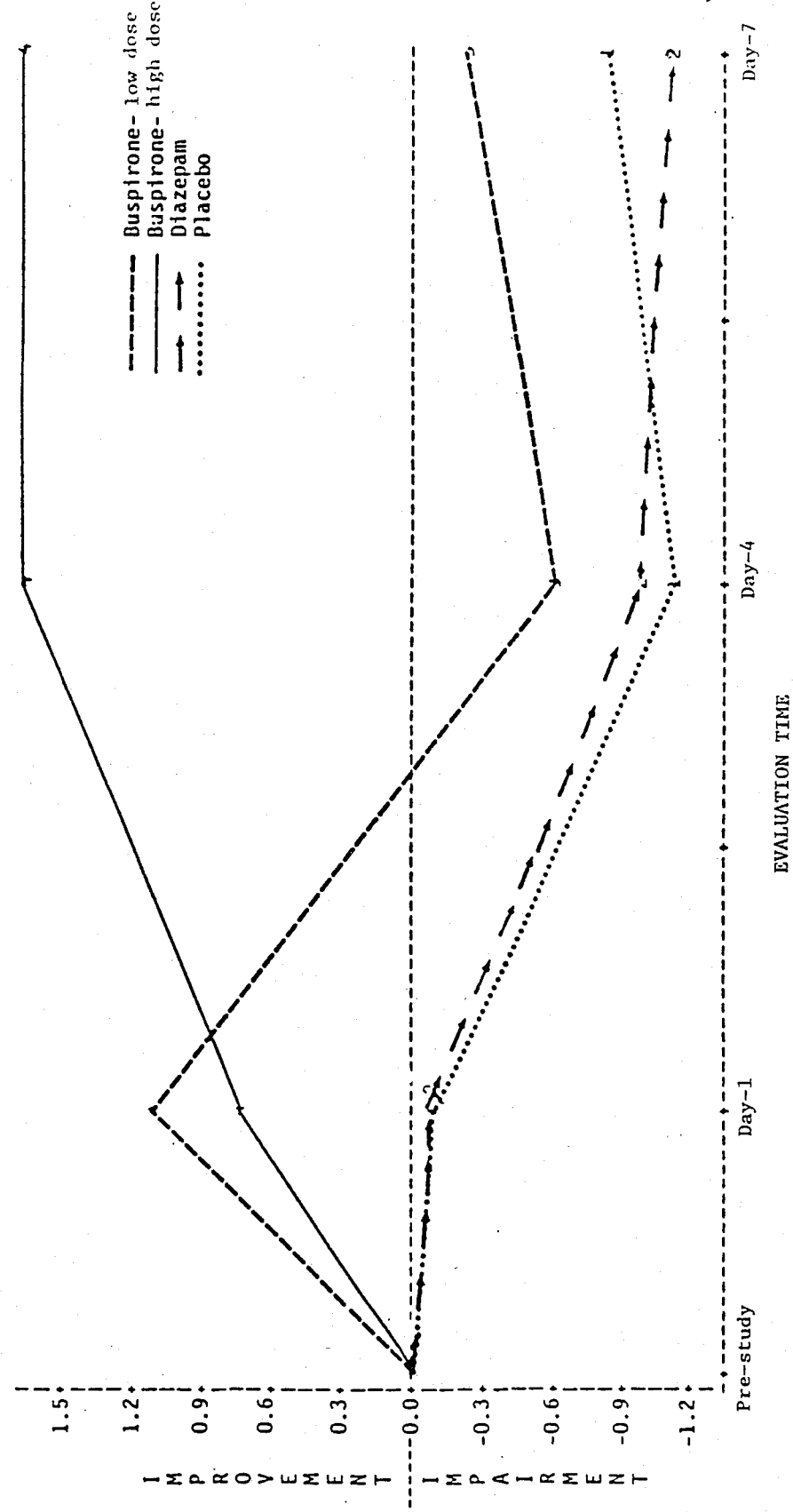
FIG. 1 depicts immediate recall scores, which reflect short term memory, and these scores are displayed as mean changes from baseline scores.

Results obtained for immediate recall are shown in FIG. 1. The baseline value for each treatment group was determined by finding the mean value for the patient scores for each treatment group at the pre-study time point. Subsequent change in score during the time course of the study is shown in FIG. 1 as a change from baseline score for that particular group. On the first day of drug treatment (at about 1 hour after drug administration), there was a tendency for the buspirone groups to show improved memory from their baseline values. On day 4, the high dose buspirone group was improved both in regard to its baseline and other groups, but the low dose buspirone group was not much different from the other groups. Results on day 7 were essentially the same as those on day 4. The other treatment groups demonstrated a tendency toward impairment from control values.

Figure 2:
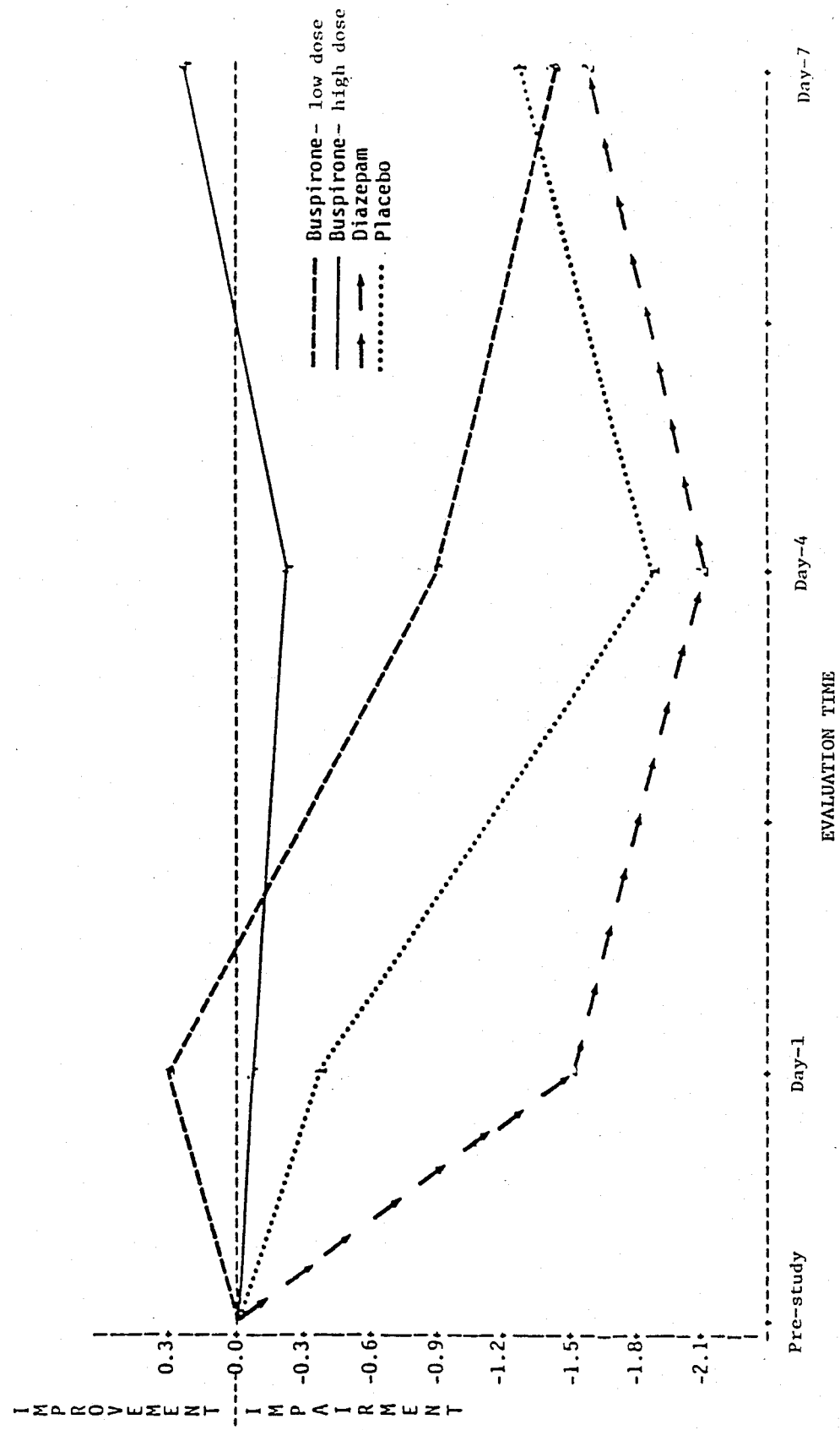
In FIG. 2, depicting delayed memory, recall scores are displayed as mean changes in test scores, again compared with the pre-study baseline score for each group. As before, the high dose buspirone group recorded higher scores at days 4 and 7 compared with the other treatment groups.

A somewhat different pattern was observed for results of delayed recall testing, as shown in FIG. 2. Diazepam demonstrated significant impairment from its control value at all three time periods—days 1, 4 and 7. The placebo group was also significantly impaired on days 4 and 7. The low dose buspirone group showed impairment on day 7. In contrast, the high dose buspirone group demonstrated no sign of impairment in mean score throughout the study.

In summarizing results of the memory tests, the results indicate that buspirone improves memory. This was most clearly demonstrated in immediate recall testing for the high dose buspirone group. Due to the large spread in individual test scores and the small number of patients in each treatment group, there was no overall significant difference ($p < 0.05$) between any of the treatment groups at any given time point. While statistical significance was not achieved for the buspirone groups, the data do suggest a higher level of memory performance in these treatment groups compared to the diazepam and placebo groups. If, for some reason, the conditions of the study led to a decreased recall over the study period for all patients (note the decrease of score value with time for the placebo group), it could be inferred that even more of an increase in immediate recall would have been observed with buspirone had this memory decay tendency not been present. It is also not unreasonable to expect that a more robust effect on memory improvement might be seen with higher doses of buspirone.

The process then of the present invention essentially involves administration of buspirone, or a pharmaceutically acceptable acid addition salt thereof, to a patient in need of such treatment. Pharmaceutically acceptable acid addition salts of buspirone and methods of pharmaceutical formulation are described in the above patents of Wu, et al., and Casten, et al., both of which have been referred to earlier and were incorporated by reference. It is also to be noted that buspirone is structurally unrelated to any agent which has been reported to bring about improvement of memory. In addition, none of the other uses disclosed previously for buspirone would in any way teach its use in memory improvement.

Administration of buspirone according to the present invention may be made by the parenteral, oral, sublingual or rectal routes; as well as by nasal or dermal application. The oral route is preferred, however. The clinical dosage range for improvement of short-term memory is expected to be about the same to slightly higher compared with the dose recommended for anti-anxiety usage, but can vary to some extent. In general, the expected amount of buspirone administered would be less than about 100 mg/day, generally in the range of about 30–80 mg with about 20–60 mg being preferred. Since the dosage should be tailored to the individual patient, the usual practice is to commence with a dose of about 5–10 mg administered two or three times per day and then to increase the dose every two or three days by 5 mg at each dosage time until the desired response is observed or until the patient exhibits side effects. Single daily dosage may be applicable in some instances.

What is claimed is:

1. A method for improving short term memory which comprises administering a non-toxic therapeutically effective dose of buspirone or a pharmaceutically acceptable acid addition salt thereof to a patient in need of such treatment.

2. The method of claim 1 wherein buspirone hydrochloride is employed and dosage is by the oral route.

3. The method of claim 1 wherein the patient is also afflicted with a generalized anxiety disorder.

4. The method of claim 2 wherein the patient is also afflicted with a generalized anxiety disorder.

5. The method of claims 1, 2, 3, or 4 wherein said patient is an adult and a daily dose of from about 20 to 60 mg of buspirone hydrochloride is employed.

6. The method of claim 5 wherein said daily dose is divided and administered b.i.d.

7. The method of claim 5 wherein said daily dose is divided and administered t.i.d.

* * * * *